(12) United States Patent
Podoleanu et al.

(10) Patent No.: US 7,417,741 B2
(45) Date of Patent: Aug. 26, 2008

(54) TRANSMISSIVE SCANNING DELAY LINE FOR OPTICAL COHERENCE TOMOGRAPHY

(75) Inventors: Adrian Gh. Podoleanu, Canterbury (GB); John A. Rogers, Canterbury (GB)

(73) Assignee: OTI Ophthalmic Technologies Inc. (CA)

( * ) Notice: Subject to any disclaimer, the term of this patent is extended or adjusted under 35 U.S.C. 154(b) by 92 days.

(21) Appl. No.: 11/216,403

(22) Filed: Aug. 31, 2005

(65) Prior Publication Data

US 2006/0055938 A1    Mar. 16, 2006

(30) Foreign Application Priority Data

| Sep. 1, 2004 | (GB) | .................. | 0419383.5 |
| Jul. 6, 2005 | (GB) | .................. | 0513773.2 |

(51) Int. Cl.
*G01B 9/02* (2006.01)

(52) U.S. Cl. .................................. 356/479; 356/497

(58) Field of Classification Search ................ 356/479, 356/497

See application file for complete search history.

(56) References Cited

U.S. PATENT DOCUMENTS

| 5,321,501 | A | * | 6/1994 | Swanson et al. ............ 356/479 |
| 5,975,697 | A | | 11/1999 | Podoleanu et al. |
| 6,111,645 | A | | 8/2000 | Tearney et al. |
| 6,282,011 | B1 | | 8/2001 | Tearney et al. |
| 6,421,164 | B2 | | 7/2002 | Tearney et al. |
| 6,564,089 | B2 | | 5/2003 | Izatt et al. |
| 6,769,769 | B2 | | 8/2004 | Podoleanu et al. |

(Continued)

OTHER PUBLICATIONS

Tearney et al, High-speed phase- and group-delay scanning with a grating-based phase control delay line, Optics Letters, Dec. 1997, pp. 1811-1813.*

(Continued)

*Primary Examiner*—Samuel A Turner
(74) *Attorney, Agent, or Firm*—Lawrence E Laubscher, Jr.

(57) ABSTRACT

A scanningdelay line for use in optical coherence tomography apparatus has a tiltable mirror, and optical convergence means for converging light incident, a dispersive element for dispersing light incident, and an optical-redirector for changing the direction of an icident beam light. The tiltable mirror, optical convergence element, said dispersive element, and optical redirector means are arranged in an optical configuration such that in sequence the dispersive element directs an input beam toward the optical convergence element, the optical convergence element directs the input beam toward the tiltable mirror, the tiltable mirror reflects the input beam as a first return beam toward the optical convergence element, the optical convergence element directs the first return beam toward the dispersive element, the dispersive element directs the first return beam toward the redirector, and the redirector redirects the first return beam toward the tiltable mirror via the optical convergence element in a direction such that the tiltable mirror reflects the first return beam toward the optical convergence optics element as a second return beam and the optical convergence element directs the second return beam toward the output port as part of an output beam bypassing the dispersive element and such that the output beam lies along substantially the same axis regardless of the angle of tilt of said tiltable mirror. The tilting said mirror varies introduces a variable optical delay into said output beam between the input and output pods. The delay line can be used in the transmission one of the arms of OCT interferometers, resulting in reduced walk-off and loss.

32 Claims, 11 Drawing Sheets

U.S. PATENT DOCUMENTS

2003/0137669 A1    7/2003    Rollins et al.

OTHER PUBLICATIONS

Podoleanu et al, Three dimensional OCT images from retna and skin, Optics Express, Oct. 2000, pp. 292-298.*

Moger et al, Develodement of a phase-resolved DOCT system for use in cutaneous microcirculation research, Proceedings of the SPIE, vol. 4619, 2002, pp. 269-275.*

Bourquin et al, Ultrahigh resolution real time OCT imaging using a compact femosecond Nd: glass laser and nonlinear fiber, Optics Express, Dec. 2003, pp. 3290-3297.*

Kwong, K.F., et al, "400-Hz Mechanical Scanning Optical Delay Line," Journal, Oct. 26, 1992, pp. 558-560, vol. 18 No. 7, Optical Society of America, USA.

Podoleanu, Adrian GH., et al, "Transversal and Longitudinal Images from the Retina of the Living Eye Using Low Coherence Reflectometry," Journal, Jan. 1998, pp. 12-20, vol. 3 No. 1, Journal of Biomedical Optics, United Kingdom.

Rollins, Andrew M., et al, "In vivo Video Rate Optical Coherence Tomagraphy," Journal, Sep. 14, 1998, pp. 219-229, vol. 3 No. 6, Optical Society of America, USA.

* cited by examiner

TRANSMISSIVE SCANNING DELAY LINE FOR OPTICAL COHERENCE TOMOGRAPHY

FIELD OF THE INVENTION

The invention refers to the field of path scanning, optical measurements, and more specifically to the field of high resolution optical imaging by means of optical coherence tomography.

BACKGROUND OF THE INVENTION

Optical coherence tomography (OCT) is an interferometric imaging technique described, for example, in U.S. Pat. No. 5,975,697. In order to produce OCT scans in the depth direction, the optical path length between a reference beam and object is varied, which requires a technique for progressively varying an optical path length.

Different depth scanning procedures have been devised to be incorporated into optical coherence tomography set-ups. One of the most successful procedures uses the introduction of a phase term linearly dependent on the optical frequency. The Fourier transformation leads to an equivalent optical path. The method is inspired from research on processing of femtosecond pulses, as described in the paper "400 Hz mechanical scanning delay line", published in Opt. Letters, Vol., 18, No. 7, 1993, pages 558-560, by K. F. Kwong et al. The method has the added advantage of allowing for dispersion compensation. Known under the name of spectral delay line, the method uses a diffraction grating, a lens and a galvanometer scanner, as disclosed in U.S. Pat. No. 611,645, Grating based phase control optical delay line by, G. Tearney, E. Bouma, J. Fujimoto and by U.S. Pat. No. 6,421,164 by, G. Tearney, "Interferometeric imaging with a grating based phase control optical delay line", U.S. Pat. No. 6,282,011B1. The linear variation of phase versus optical frequency is introduced by tilting a galvanometer mirror behind a lens, where the galvanometer mirror is situated in the Fourier plane of the lens. Tilting the mirror causes the returned beam to be deviated from the grating along a direction parallel to the incident beam. Usually, OCT configurations use reflective set-ups, where the same fiber aperture is employed in launching light towards and from the depth scanning device. This means that during scanning in depth, the amount of light re-injected back into the fiber aperture varies, i.e. the beam walks off the main direction (where the loss is at a minimum). This phenomenon is known as walk-off.

US patent publication no. 20030137669A1, by A. M. Rollins, "Aspects of basic OCT engine technologies for high speed optical coherence tomography and light source and other improvements in optical coherence tomography" describes a technique for reducing walk-off wherein a mirror is added to return the beam back to the scanning delay line, the beam is re-circulated four times via the diffraction grating which finally leads to a de-scanning of the lateral movement of the output beam.

Such configurations have been devised to operate in transmission as well, where a different fiber aperture is used to capture the output beam, as disclosed in the U.S. Pat. No. 6,564,089 B2, by J. A. Izatt, "Optical Imaging Device". However, this transmissive scanning delay line descans the beam by four time diffraction off the diffraction grating which leads to losses of the optical beam. It will be desirable if the high loss element such as the diffracting grating is used less in the configuration.

It would also be desirable to combine optimally the scanning depth capability of such devices with that of transversally scanning the beam in order to obtain a versatility of scanning modes in generating OCT images and reconstruct the 3D volume of a scattering volume, such as that of a biologic or industrial sample.

SUMMARY OF THE INVENTION

According to the present invention there is provided a scanning delay line comprising convergence optics for converging light incident thereon; dispersive optics for dispersing an incident light beam via said convergence optics toward tiltable mirror means which redirects said light beam back via said convergence optics toward dispersive optics for dispersing the light beam a second time; and a redirecting arrangement for redirecting said light beam back via said convergence optics after said light beam has been dispersed a second time toward tiltable mirror means which redirects said light beam back via through said convergence optics into an output beam; and wherein tilting said tiltable mirror means varies the optical path length for said light beam within the delay line.

The convergence optics can be provided by a common lens or mirror. Alternatively, it can comprise separate optical elements. The same is true for the dispersive optics and the tiltable mirror means, which can comprise a common facet of the tiltable mirror or opposite facets of the tiltable mirror.

In this specification, the terms "light" and "optical" are not intended to restrict the invention to visible wavelengths, but include other wavelengths, such as infrared, having similar properties.

In a first aspect, the present disclosure shows how the walk-off can be reduced and the beam de-scanned by using dispersion elements, such as a prism or a diffraction grating twice only, or two such dispersion elements, each once. This results in a reduction of losses of half of those of previously known configurations that employ the diffraction grating four times. In a second aspect, the disclosure shows how to utilise the scanning delay line in combination with transverse scanners to generate a versatility of scanning modes in order to perform with the same system 1D reflectivity profiles and 2D maps.

In a third aspect, the invention shows how to combine any scanning delay line, including that disclosed here, in tandem with other means for scanning in depth to generate B and C-scan OCT images.

In yet another aspect the invention provides a method of varying the optical path length of an incident light beam through a scanning apparatus, comprising optically dispersing the incident light beam; optically converging the dispersed light; angularly scanning the converged dispersed light; optically deconverging the angularly scanned light; optically dispersing the deconverged light; redirecting the dispersed deconvergent light; reconverging the redirected dispersed deconvergent light; angularly descanning the reconverged light; and deconverging the descanned light into an output beam; and wherein said angular scanning results in a variation of the optical path length of said incident light beam through the scanning apparatus.

BRIEF DESCRIPTION OF THE DRAWINGS

The above and further advantages of the present invention may be better understood by referring to the following drawings.

DETAILED DESCRIPTION

Figure 1:
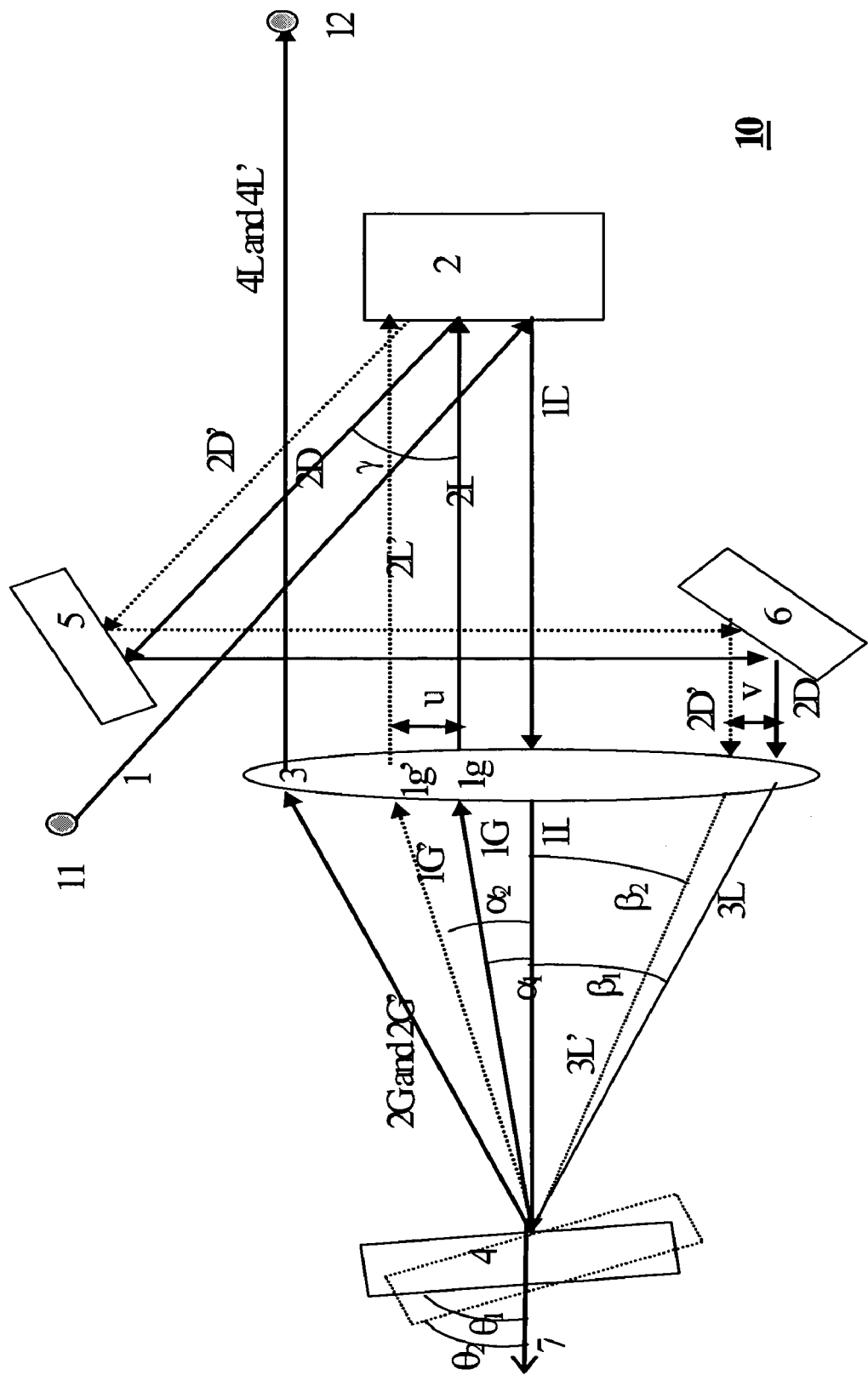
FIG. 1 is a detailed diagram of an embodiment of the invention.

As shown in FIG. 1, a collimated input beam 1, from input aperture 11, is diffracted by a diffraction grating, 2, the diffracted beam, diffracted once, 1D, passes through a lens, 3, and the beam refracted once, 1L, is sent towards a galvanometer scanner, 4. The light reflected once from the galvanometer scanner 4, beam 1G, makes the angle $\alpha_1$ with the optic axis 7, is refracted second time by the lens, 3, beam 2L, towards the diffraction grating, 2. The beam is de-scanned by the grating, so diffracted second time, 2D, into a beam parallel with the input beam, 1. The distance between the diffraction grating 2 and the lens 3 is preferably the focal length of the lens, similarly the distance between the lens 3 and the galvomirror 4 is preferably the focal length of the lens 3.

Rotating the galvanometer scanner 4, leads to deviation of the beam parallel with itself, as shown by the beam 2D'. To de-scan the beam and insure that the returned beam does not oscillate transversally, the beam 2D is redirected via mirrors 5 and 6 through the lens 3, $3^{rd}$ time refracted, beam 3L, back towards the galvanometer mirror at an angle $\beta_1$ with axis 7, wherefrom is reflected $2^{nd}$ time, beam 2G The beam is then refracted $4^{th}$ time, into the output beam 4L, towards the output aperture 12. The input and output apertures 11 and 12 could be a lens or a curved mirror launching and respectively receiving collimated beams. Such apertures consist in at least a lens or a curved mirror grouped with a pinhole or optical fibre. In the input aperture, the pinhole or fibre launch the beam towards the lens or curved mirror while in the output aperture, pinhole or fiber receive the output beam 4L. The input and output apertures are not shown here as they are parts of the interferometer where the transmissive scanning line will be incorporated. For the operation of the scanning delay line it is essential that the beam from the input aperture is collimated and that the beam 4L hits the output aperture irrespective of the angle θ. Any lateral deviation (walkoff) of the beam 4L results in stray intensity modulation Let us consider the galvanometer scanner mirror, 4, tilted as shown by the dashed line, making angle $\theta_2$ with the axis 7, different than $\theta_1$ before. Due to the galvanometer tilt, the beam 1G becomes 1G', making the angle $\alpha_2$ with the axis 7, 2L becomes 2L' and as mentioned before, irrespective of the scanner angle, the beam diffracted from the diffraction grating second time, 2D', is parallel with the incident beam, 1. Now 2D' generates a beam 3L' at an angle $\beta_2$ with the axis, 7, smaller than $\beta_1$, but similar to the angle with the scanner mirror 4, to that made by the rays 3L. Consequently, the resulting reflected beam 2G' superposes on the beam 2G and the output beam 4L' ideally superposes the initial beam 4L and no walk-off is registered. The rays for the angle $\theta_2$ are shown in dashed line.

A close analysis of ray tracing through the system suggests optimisation of the configuration for best attenuation of the walkoff. The walkoff is in practice given by the distance between points 1g and 1g', u, where the two rays for two tilting angles, $\theta_1$ and $\theta_2$ of the mirror 4 reach the lens 3. By rerouting the two rays via the scanner mirror 4, the corresponding points where the rays 2G and 2G' reach the lens should be as close as possible. When rays 2G and 2G' are exactly superposed, as shown in FIG. 1, walkoff is ideally removed. The distance, u, evolves along propagation through the delay line by two effects in FIG. 1.

a. Lateral deviation, u, depends for the same differential scanning angle tilt, $\alpha_2 - \alpha_1$, on the deviation of angles 1G and 1G', $\alpha_1$, $\alpha_2$, from the axis.

$$u/f = \tan\alpha_2 - \tan\alpha_1 = \frac{\sin(\alpha_2 - \alpha_1)}{\cos\alpha_2 \cos\alpha_1} \quad (1)$$

The same could be written for the relative distance v between the two rays 2D and 2D', before being injected into the lens for the $3^{rd}$ time:

$$v/f = \tan\beta_2 - \tan\beta_1 = \frac{\sin(\beta_2 - \beta_1)}{\cos\beta_2 \cos\beta_1} \quad (2)$$

The equations show that for the same differential tilt $\alpha_2 - \alpha_1 = \beta_2 - \beta_1$ (condition required for walkoff elimination), u and v are different.

$$u/v = \frac{\cos\beta_2 \cos\beta_1}{\cos\alpha_2 \cos\alpha_1} \quad (3)$$

Because the angles $\alpha_1$ and $\alpha_2$ are smaller than $\beta_1$ and $\beta_2$, u<v. Cancellation of walkoff requires that for $\alpha_2 - \alpha_1 = \beta_2 - \beta_1$, $$u<v. \quad (4)$$

However, due to the second effect, diffraction, u>v.

b. Diffraction on grating 2, transfers the distance u between the two incoming beams 2L and 2L' into a smaller distance v, due to the angle γ, between the incident ray on the grating and the diffracted ray:

$$v = u \cos \gamma$$

which shows that $$u>v \quad (5).$$

Different solutions are possible to address these two problems. The simplest solution consists in amplifying the projection of distance v along the lens direction, to increase v and satisfy equation (4). This is achieved by rotating the mirror 6, or equivalently the mirror 5, to deviate the rays 2D and 2D' to the bottom edge of the lens 3. In this way, not only the projection along the lens is longer, but the angles $\beta_1$ and $\beta_2$ become smaller. This may have the result of beams 3L and 3L' falling in points different from the point where the ray 1L hits the mirror 4. A move towards the bottom of the FIG. 1 of the point where the 3L and 3L' hit 4 supplementary lead to reduction of angles $\beta_1$ and $\beta_2$ as a positive effect. It should be taken into account that the ray 4L now may emerge not parallel with the ray 1D. This is compensated by a corresponding orientation of the output aperture, 12.

This method however is limited, as by tilting the mirror 6 too much, the emergent rays 2G and 2G' may hit the diffraction grating 2.

In respect to the $2^{nd}$ problem, the change of distance between the extreme rays during scanning during the traversal of the dispersive element, this can be addressed by tilting it. In FIG. 1, by tilting the diffraction grating, it could be possible even to make v>u. However, this solution is also limited due to variation of dispersion during scanning when the grating normal is not aligned to the emergent beam direction.

Those skilled in the art with the benefit of this disclosure will realise that the lens 3 could equally be implemented using a mirror and the diffraction grating 2 using a prism. Therefore examples are incorporated here using mirrors and prisms.

By altering the distance between the grating 2 and the lens 3, controlled dispersion in the system could be introduced.

Figure 2:
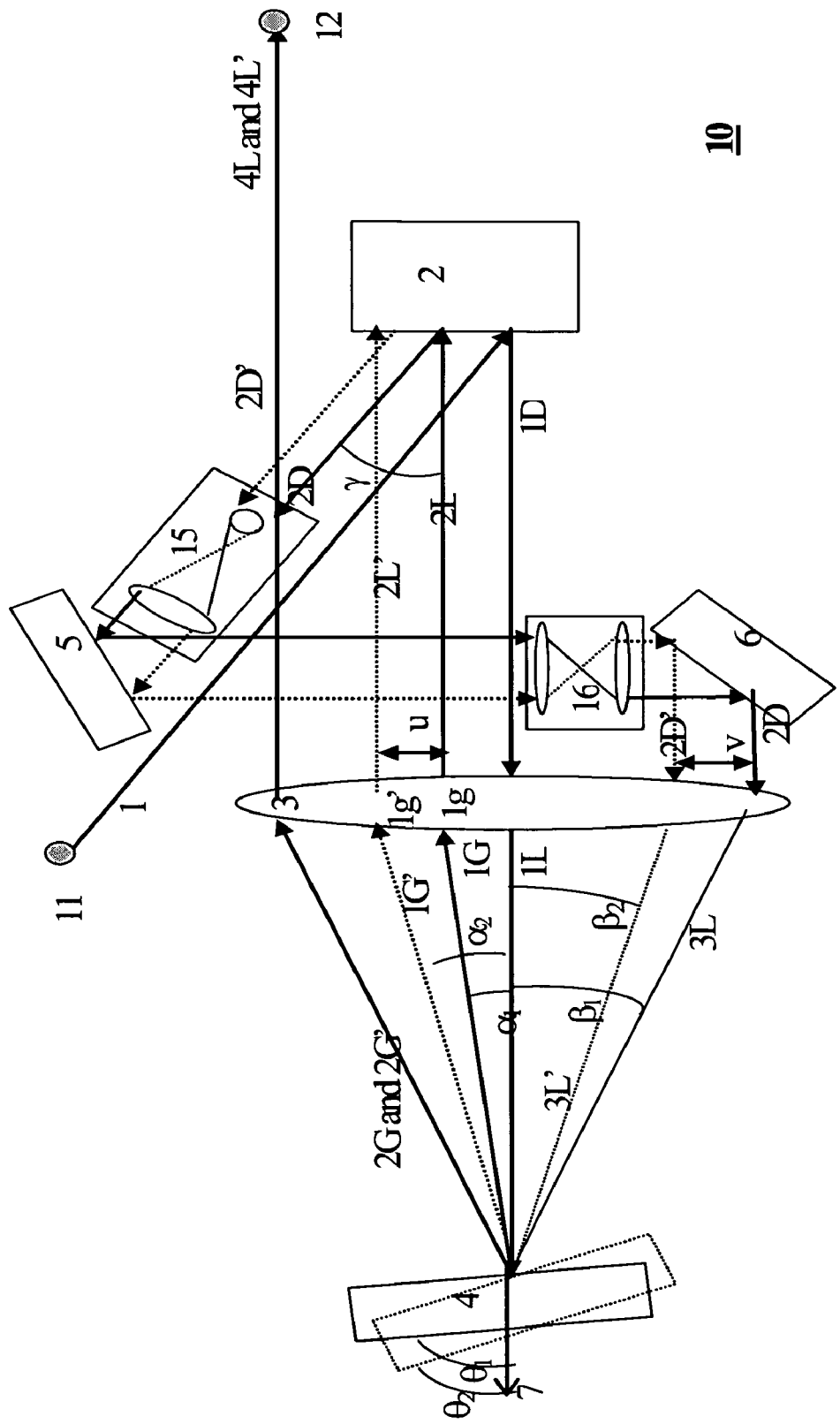
FIG. 2 shows a different version of the embodiment of the invention in FIG. 1

FIG. 2 shows another embodiment of the transmissive scanning delay line, where to further reduce the walkoff, two telescopes, 15 and 16 are used between the dispersion element, the diffraction grating, 2 in FIG. 1 and the mirror 6. The telescopes have two functions: (1). to enlarge the diameter of the beam, v, before being launched into the lens 3; (2) to place the rays 2D' and 2D in the same relative position as that without telescopes. In FIG. 2, telescope 15 enlarges the beam diameter but reverts the relative placement of the beams 2D and 2D' Therefore, a second telescope 16 is required to swoop the two rays laterally. Evidently, the enlargement power could be distributed on both telescopes. Also, the telescopes could be implemented using curved mirrors, and only as an example they are shown using lenses in FIG. 2, and concave and convex lenses could be used alike. Also, the 4 lenses of the two tescopes could be distributed interleaved with the mirrors 5 and 6, for instance mirror 5 and mirror 6 could be in between the pair of lenses in the telescope.

Magnification of u into v could be as large as required to address both problems mentioned above.

Figure 3:
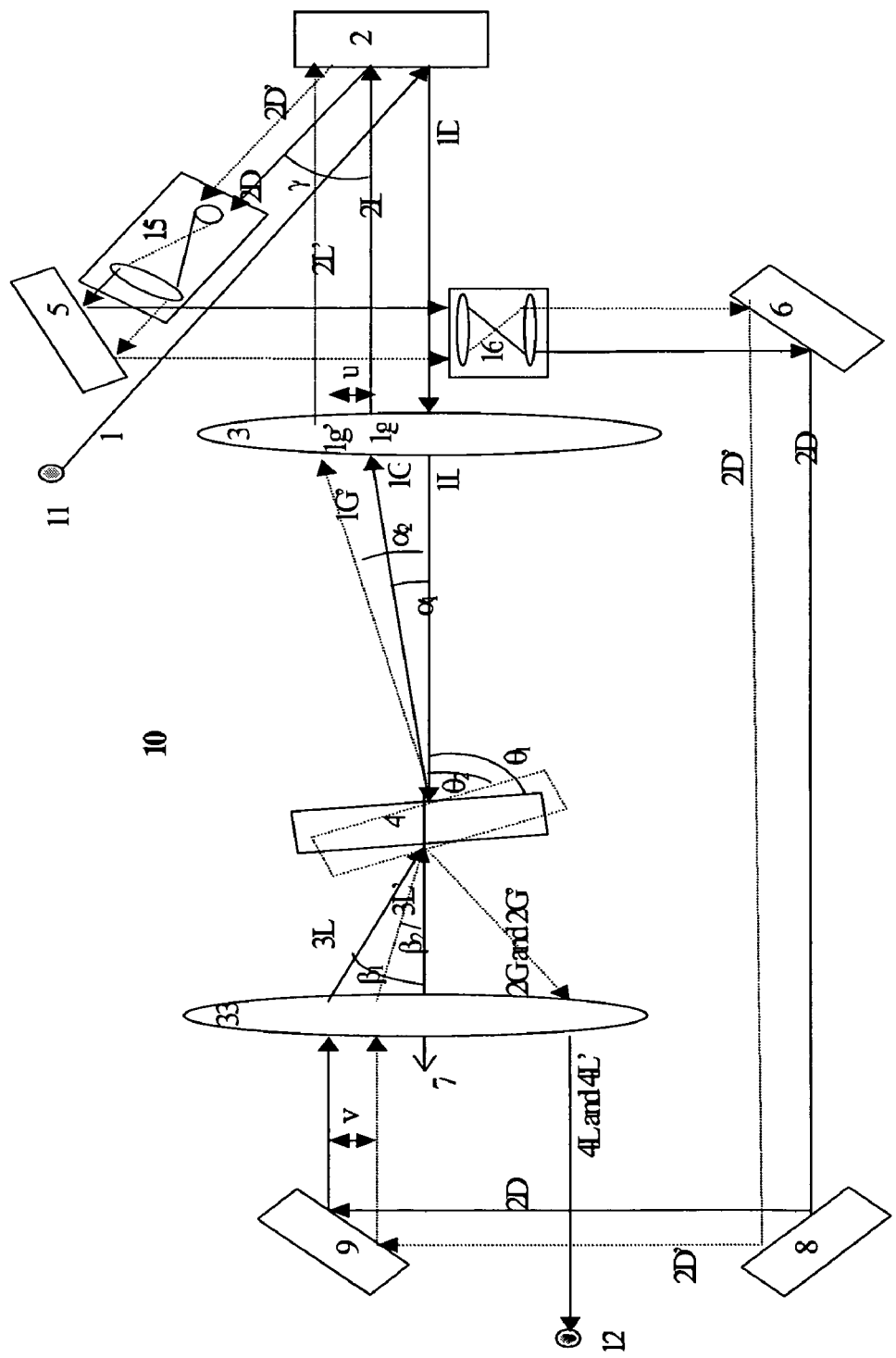
FIG. 3 is a detailed diagram of another embodiment of the invention.

FIG. 3 shows another embodiment of the transmissive scanning delay line, where to further reduce the walkoff, a separate lens, 33, is employed and the other facet of the scanning mirror 4. Light from mirror 6, is sent via two mirror 8 and 9 towards a second lens, 32. In comparison with FIGS. 1 and 2, the rays 3L and 3L' hit the galvo-mirror 4 from the other side. Rays 3L makes a larger angle, $\beta_1$ with the optic axis than the ray 3L', $\beta_2$, and when routed via the galvo-mirror 4, shown in the two positions, solid line for deflecting the ray 1G along $\alpha_1$ and dashed line, for deflecting the ray 1G' along $\alpha_2$, deflects rays 3L and 3L' into similar direction shown by 4L and 4L'. The advantage of the embodiment in FIG. 3 in comparison with the other two embodiments is due to the fact that $\beta_1$ and $\beta_2$ can be made smaller than the angles $\alpha_2$ and $\alpha_1$. This is possible because there is no obstruction in the central part of the lens 33. Obviously, as mentioned before in connection with the other two embodiments, the matching of deviations due to scanning, u and v could be performed by one of the methods: (i) tilting one of the mirrors, 5, 6, 7 and 8, to reduce the angles $\beta_1$ and $\beta_2$; (ii) by tilting the grating and (iii) by using telescopes, 15 and 16.

The lens 33 could also be placed in the same plane with lens 3, if the scanner mirror is extended to cover more than the sum of radiuses of the two lenses 3 and 33 and the rays 2D and 2D' are taken out of the initial plane and moved parallel with themselves in a plane perpendicular to that of the drawings in FIG. 2 and on the axis of the lens 33, using mirrors 8 and 9. The lens 33 could be different from lens 3, the only requirement being that the distance from galvo-mirror to the lens 33 is equal to the focal length of lens 33. Similarly, the embodiment in FIG. 3 admits replacing the diffraction grating with a prism.

Figure 4:
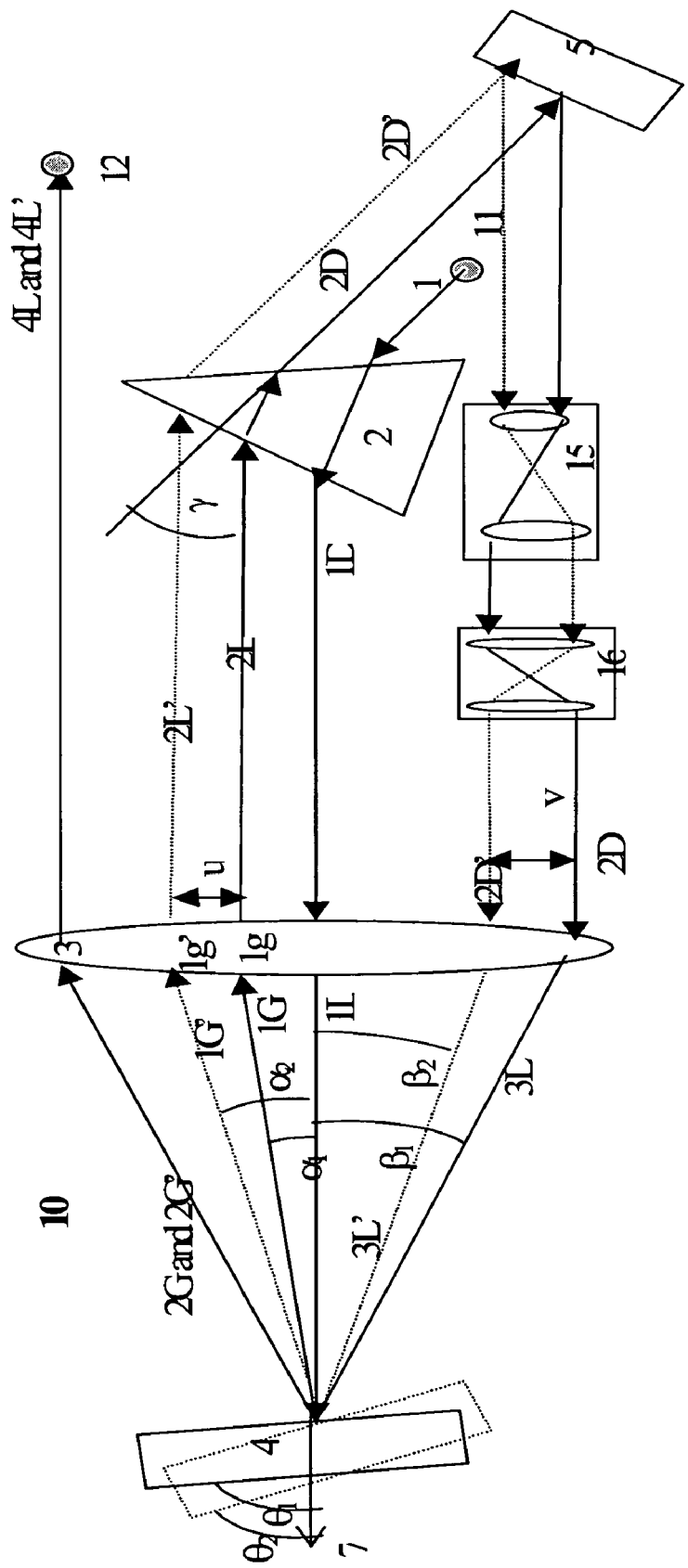
FIG. 4 shows a different version of the embodiment in FIG. 2 using a prism as the dispersion element.

FIG. 4 shows a version of the embodiment in FIG. 2 where the dispersion element 2 is a prism. Depending on the inclination of the prism, different relations between u incident on the prism and v for the rays traversing the prism can be obtained. Again, the prism is traversed twice which leads to less complexity and losses than traversing it 4 times.

Figure 5:
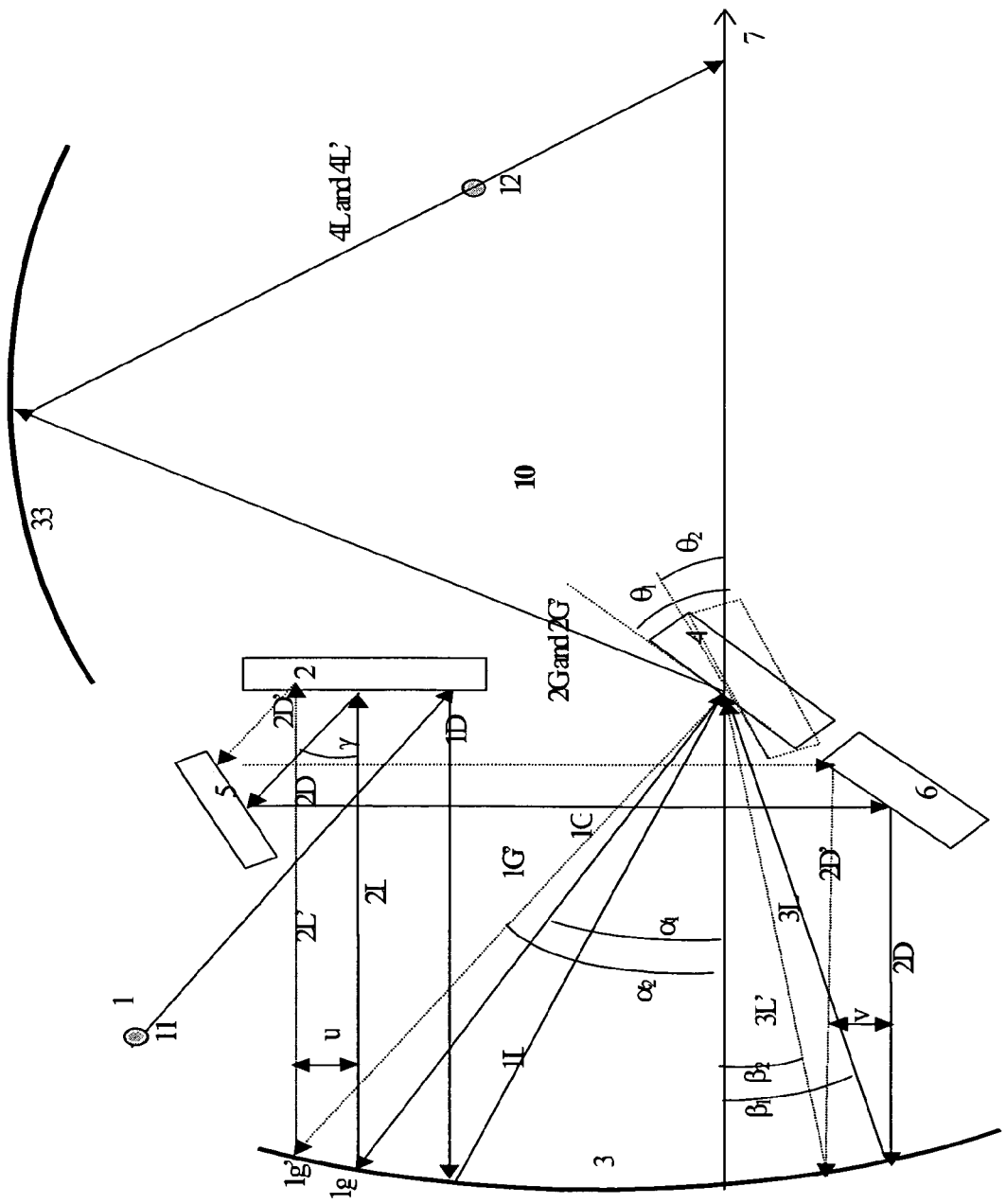
FIG. 5 shows a different version of the embodiment in FIG. 3 using spherical mirrors instead of lenses.

FIG. 5 shows another embodiment of the transmissive scanning delay line, where two spherical mirrors, 3 and 33, are used instead of lenses. The number of passes through the dispersion element is two and mirror 3 is used three times while mirror 33 once, so again there are 4 passes on the curved mirrors instead of 4 passes through the lens. The significance of notation is the same as in FIGS. 1, 2 and 3, where 1L, 2L, 3L and 4L mean rays which have been reflected by the mirrors once, twice, triple and quadruple times respectively.

Figure 6:
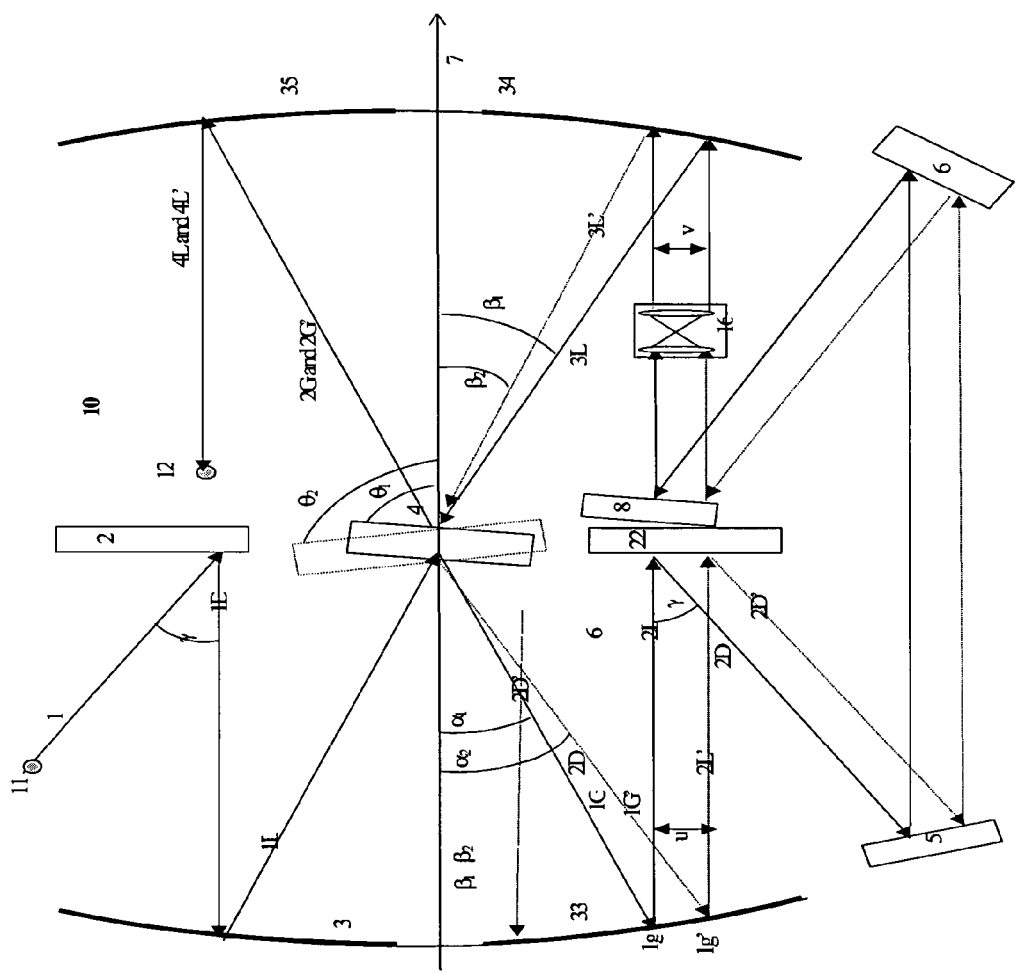
FIG. 6 shows another embodiment of the invention.

FIG. 6 shows another embodiment of the transmissive scanning delay line, where the diffraction grating has two parts, 2 and 22, and two to four spherical mirrors are used. Each diffraction grating is traversed once, i.e the total dispersion events is still two, in the spirit of the present invention. As shown by the thin line behind, mirrors 3 and 33 could be parts of the same mirror and 34 and 35 could also be parts of the same mirror. For ease of adjustment, it is preferable to use one mirror for 3 and 33 and another separate mirror for 34 and 35, also for the grating 22 to be similar to grating 2. As shown in FIG. 6, the grating 22 is rotated by 180 degrees to diffract the rays outside of the embodiment (i.e. to the bottom fo FIG. 6), the same angle $\gamma$ as the angle between the incident and diffracted rays on grating 2. Mirrors 5,6, 8 and 34 are used to direct the rays towards the other facet of the galvo-mirror 4. This is also in the focus of mirror 34, so the fan of rays incident on it then diverges towards mirror 35. If adjustment is ideal, rays 2G and 2G' are oriented along identical or similar directions. Because of the orientation of grating 22 in comparison to grating 2, the rays 2D and 2D' are relatively displaced before mirror 34, and therefore, a telescope, 16 is required to revert to the initial spatial orientation of reflected rays 3L and 3L'.

It is also possible to have mirrors 3 and 33 different, and of different focal length, with the only difference that the galvo-mirror 4 has to stay in the focal plane of both mirrors. The same is valid for the mirrors 34 and 35, they could be different while maintaining the galvo-mirror 4 in the focus plane of both mirrors.

Without diverting from the scope of the invention, persons skilled in the art with the benefit of this disclosure will realize that other implementations are possible to use the galvo-mirror to descan the angular movement of rays and provide an output beam with reduced walkoff. For instance, in FIG. 1, two gratings and tow lenses could be used, where the normal to the first grating is oriented along the axis of a $1^{st}$ lens and not normal to the rotation axis of the galvanometer mirror 4. Rays 1, 1D, 1L are in the same plane. A different plane is defined by ray 1G which traverses a second lens, and is incident on a second diffraction grating, where the normal to the second grating is oriented along the axis of the second lens and not perpendicular to the axis of rotation of tiltable mirror 4, wherefrom, rays are brought to one of the two lenses or a different lens to de-scan the walkoff. In total, the dispersion events are two, one on each diffraction grating and 4 traverses through lenses, at least once through the first lens, at least once through the second lens and twice through a third lens or twice through one of the first or the second lens.

In the same way, all other embodiments could be reconfigured without deviating from the spirit of the invention of maintaining a minimum number of two for the traversal of a dispersion element and using the tiltable mirror for de-scanning the walk-off. It may also be possible to devise a combination like in FIG. 3, 5 or 6 where mirrors and lenses are used in the same set-up. It may also be possible in an embodiment like that in FIG. 6 for one dispersion element to be a grating and for the other dispersion element to be a prism.

For large band low coherence sources, focusing elements need to be replaced by mirrors and preferably mirrors need to be used. Examples were given using spherical mirrors. It should be obvious for the person skilled in the art to replace spherical mirrors with parabolic mirrors without diverting from the scope of the invention.

In all embodiments above, by moving the incidence point of ray 1L or 3L or both away from the axis of rotation of the galvoscanner 4, phase modulation is introduced in addition to the simultaneous depth scanning. Two types of phase modulation are possible. When the ray 1L is moved away, the phase modulation introduced is that predicted by Fourier theory of the spectral scanning delay line. The offset obtained by moving the ray 3L generates a phase modulation similar to the embodiments of depth scanning in U.S. Pat. No. 5,975,697.

Figure 7:
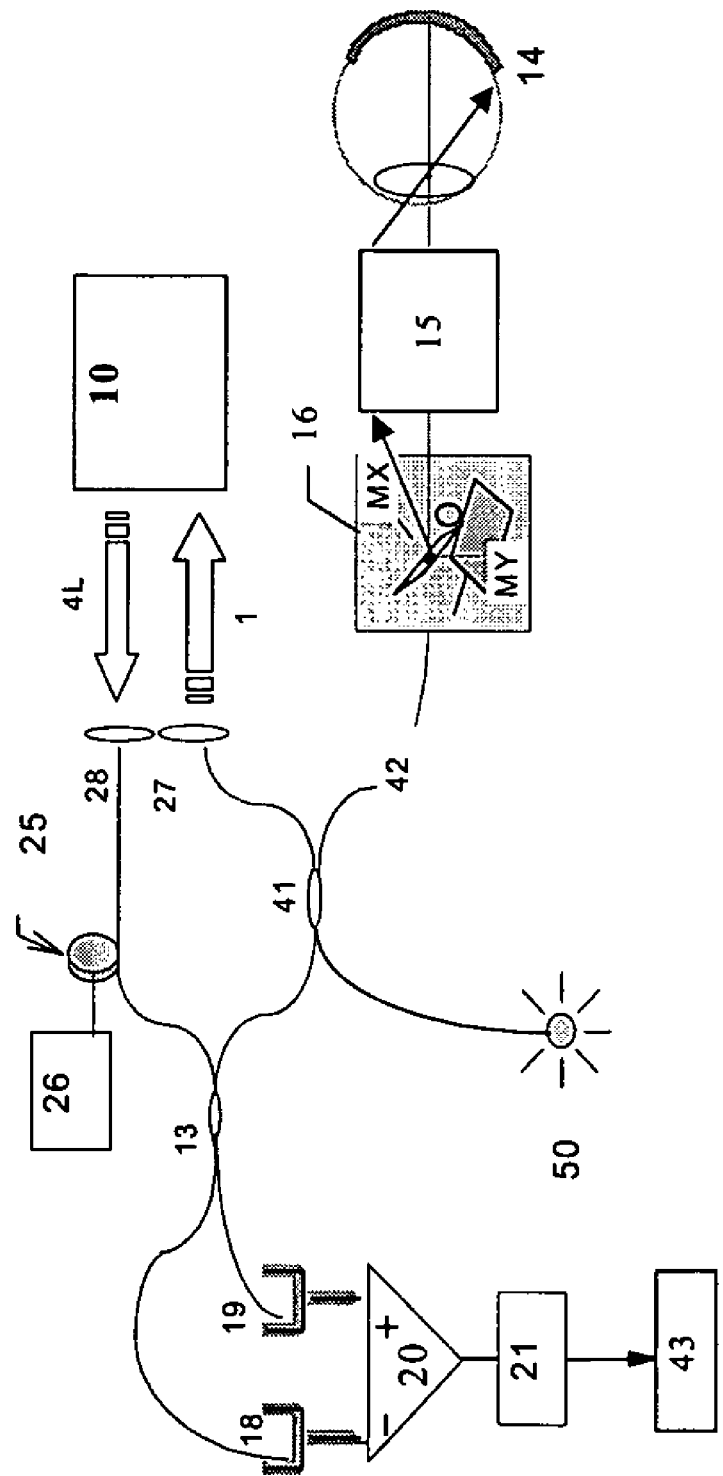
FIG. 7 shows a block diagram of a balanced OCT configuration using one of the embodiments in FIG. 1, 2, 3, 4 or 5 of the scanning delay line incorporated into its reference arm.

FIG. 7 gives an example of using the transmissive delay line in the reference arm of an OCT interferometer. Light from a low coherence source, 50, is sent via the $1^{st}$ splitter, 41 toward the object path, 42 and reference path, 1, which via the transmissive delay line, 10, reaches its output, 4L, and is injected in the $1^{st}$ port of the second splitter 13, whose $2^{nd}$ port receives light returned from the object, 14, via the interface optics, 15 and transverse scanners 16, and the $1^{st}$ splitter, 41. The configuration in FIG. 6 with re-circulating reference power is essential in order to avoid that signal from the reference path, usually strong, returns to the low coherence source, 50, prone to oscillation and even damage if light if sufficient light is returned back into the source. This configuration allows balance detection, implemented at the output of the $2^{nd}$ splitter, using two photodetectors, 17 and 19 and a differential amplifier 20. The signal is processed in the demodulator 21 and displayed and measured by the displayed measuring means 43. The incorporation of the transmissive delay line in the OCT configuration is compatible with application of phase modulation, using the a phase modulator, 25 driven by a generator, 26. The light input to the transmissive delay line is collimated using a focusing element 27, a convergent lens or a concave mirror. This forms the input aperture 11. Similarly, the output light, 41, is focused into the fiber using another focusing element 28, in the form of a convergent lens or a concave mirror. This forms the output aperture 12.

Modes of Operation

The transmissive scanning delay line can be used to generate A, B and C-scan images.

A-Scan Based B-Scan

Figure 8:
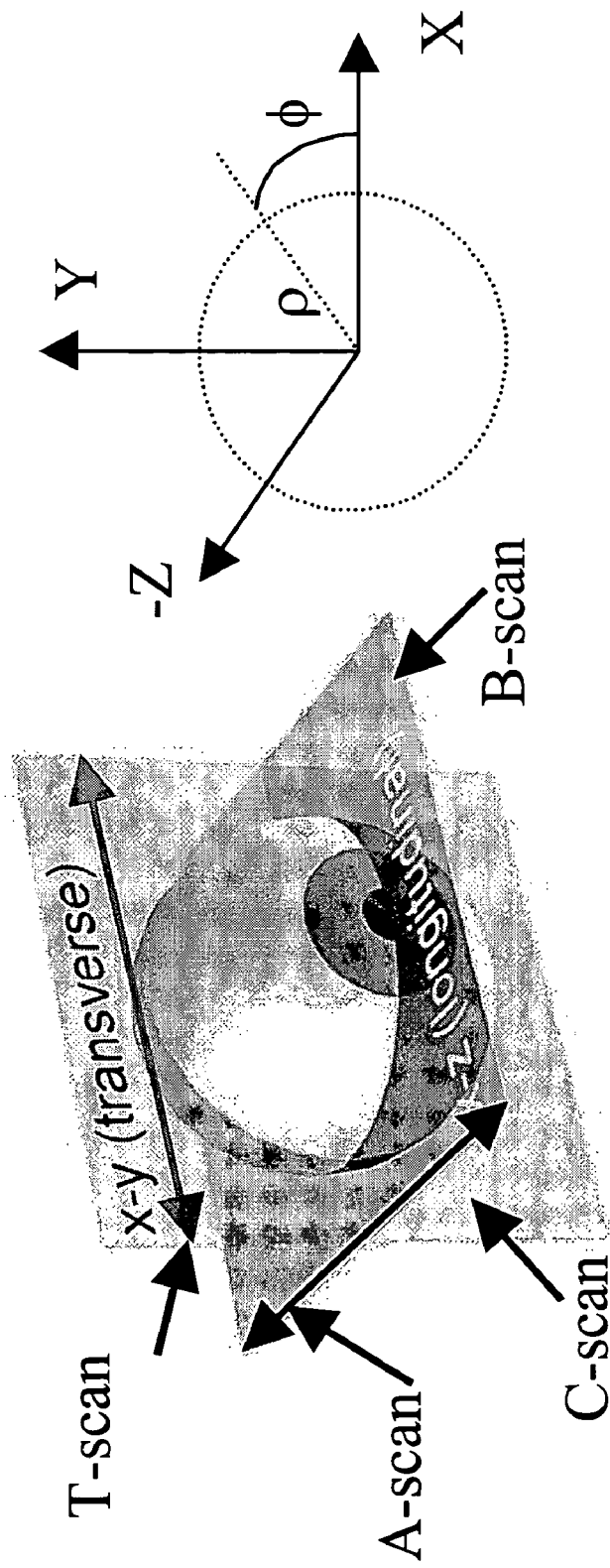
FIG. 8 is a diagram of an eye showing different scans.

The scanning delay line is used to generate A-scans. B-scan images, analogous to ultrasound B-scan are generated by collecting many such A-scans for different and adjacent transverse positions, selected by the transverse scanners. The lines in the raster generated correspond to A-scans, i.e. the lines are oriented along the depth coordinate. The transverse scanner (operating along X or Y, or along the angle θ in polar coordinates in FIG. 8, with X shown in FIG. 9 top) advances at a slower pace to build a B-scan image.

In this regime, by displacing the beam away from the axis of rotation of the tilting mirror, a high frequency carrier can be generated, which can be used to carry the square root of reflectivity of the pixel volume interrogated.

The scanning line can also be used in tandem with a phase modulator, if the beam is arranged to fall on the axis of rotation of the tilting mirror. In this case, the processing electronics after photodetection consists of band pass filtering on the phase modulation frequency, followed by a rectifier, block 21.

When referring to an external phase modulator it should be understood that one phase modulator is used or two and the phase modulation as result of beating between the two carriers applied to the two modulators is finally used in the demodulator. Two phase modulators are preferred for better compensation of dispersion by placing one modulator in the object beam and the other in the reference beam of the interferometer. Also, due to the fact that some modulators operate at high frequencies, by using two such phase modulators driven on slight different frequencies, the beating is on more amenable lower frequency values.

In case no phase modulator is used, then the band pass filter part of 21 is tuned on the carrier frequency generated by the scanning delay line, when the beam falls off the axis of rotation of the tilting mirror.

The procedures above lead to correct display of the reflectivity profile in depth, ie of A-scans for specular as well as scattering reflectors. If the scanning delay line is set on zero carrier frequency, obtained when the beam falls on the axis of rotation of the tilting mirror 4, then one fat peak is obtained for each reflector in depth. The width of the peak is determined by the coherence length of the source. The profile cannot be correctly demodulated for specular reflectors, as its amplitude depends on temperature fluctuations and could be at its maximum or its minimum. However, if the object 14 to be imaged consists of scatterers of size less than the coherence length, then several peaks are created during the depth scanning, whose envelope is the coherence length. For instance, if the coherence length is 10 microns, one peak with undetermined amplitude is obtained when the object 14 is a mirror. If the object 14 is tissue with a density of 5 scatterers per coherence length, of size less than 2 microns, then 5 or more peaks will be obtained within the same envelope of the peak for the mirror. The number of peaks depends on the shape and size of scatterers according to the scattering theory. The phase changes depending on the point of incidence of the scanning beam on the scatterer. The shape and orientation of cells, nerves, microstructures, powder, suspension in liquids, etc, determines a random characteristic of the structure of peaks generated.

The signal generated in this case is demodulated in the same way as described for the en-face scanning in the U.S. Pat. No. 5,975,697, Optical mapping apparatus with adjustable depth resolution. This patent describes operation with transverse scanners generating spikes during scanning the beam across the target 14 with the reference path fixed, and no phase modulator. As in the U.S. Pat. No. 5,975,697, a high pass filter is used to reduce the 1/f noise within the block 21. If the spikes happen at a sufficient fast rate, then a reliable information results. The larger the image size the less the distortion in the image, as the gaps between the spikes become less visible and the average of the carrier frequency so created is larger than the image bandwidth, and the larger the image size, the faster the slopes of the spikes which easier pass through the high pass filter. No external phase modulator was used to generate the images in the paper by A. Gh. Podoleanu, M. Seeger, G. M. Dobre, D. J. Webb, D. A. Jackson and F. Fitzke "Transversal and longitudinal images from the retina of the living eye using low coherence reflectometry, " published in *J. Biomed Optics*, 3, 12-20 (1998), where two band pass filters were used which combined represent a high pass filter with a low pass filter.

A similar effect happens when using the scanning delay line object of this disclosure with zero carrier frequency. If the image size, ie the depth range is sufficient large, then a correct profile in depth is obtained for a collection of scatterers, Using a high pass filter with a cut-off sufficient high to eliminate the 1/f noise, good signal to noise results. The high pass filter replaces the band pass filter in OCT embodiments tuned on the phase modulation frequency created either by an external phase modulator or using the scanning delay with the beam offset from the axis.

T-Scan Based B-Scan

Figure 9:
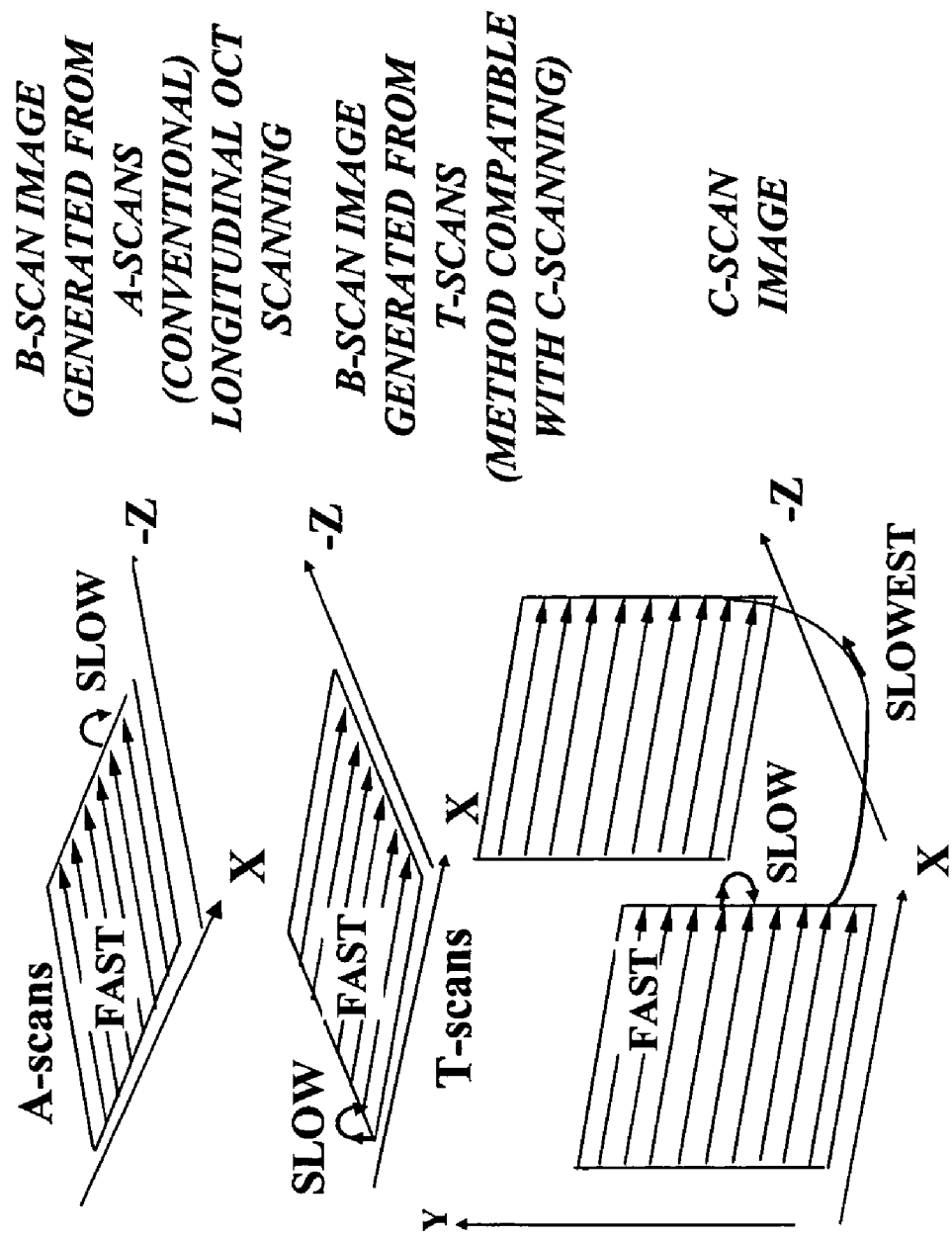
FIG. 9 shows the orientation of A, T, B and C-scans.

In this case, the transverse scanners (or scanner) 16, determine(s) the fast lines in the image; each image line is a T-scan (FIG. 9). This can be produced by controlling either the transverse scanner along the X-coordinate, or along the Y-coordinate with the other two scanners fixed (transversal fro frame and axial for depth), or controlling both transverse scanners, along the polar angle $\phi$, with the delay line scanner fixed. The example in the middle of FIG. 9 illustrates the generation of a B-scan using several T-scans, where the X-scanner produces the T-scans and the scanning delay line advances slower in depth, along the Z-coordinate. This procedure has a net advantage in comparison with the B-scan generated from several A-scans procedure as it allows production of C-scans, ie of OCT transverse (or en-face) images for a fixed reference path, as presented below.

In order to obtain a correct profile of reflectivity, ie a correct T-scan, a phase modulator is required. However, as explained in the U.S. Pat. No. 5,975,697, phase modulation by the transverse scanners 16 only could be used, especially when the object 14 is a collection of scatterers, such as tissue.

The demodulator 21 contains either a band pass filter when a phase modulator is used or a high pass filter when the phase modulation introduced by the transverse scanners is used only.

Figure 10:
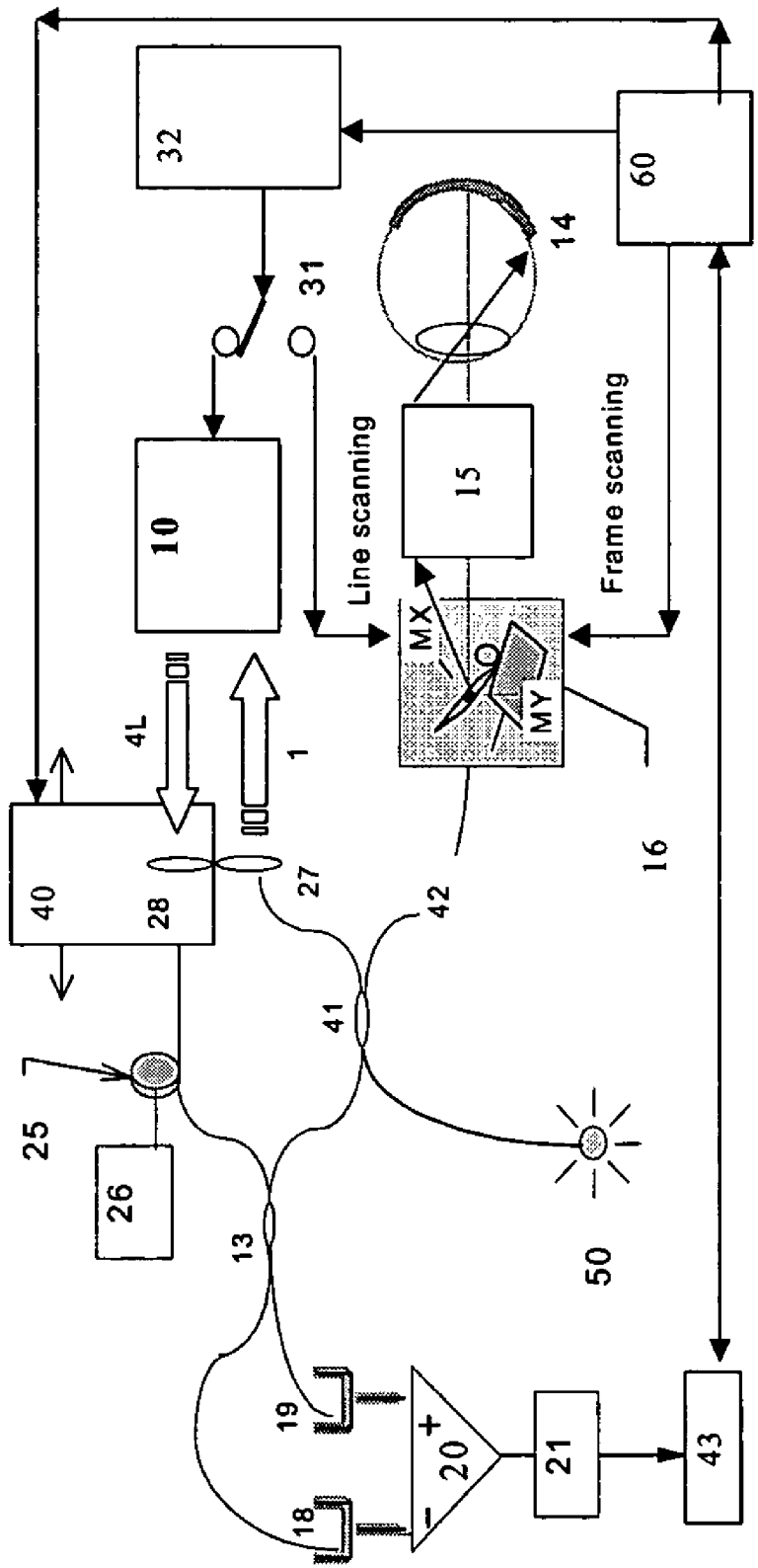
FIG. 10 shows the utilization of the transverse scanners and the scanning delay line to generate B and C scans.

It is also possible to use the scanning delay line 10 to generate the carrier, instead of using one or two phase modulators. In this case, the beam in the scanning delay line is incident off the axis of rotation of the mirror 4 and the tilting mirror 4 is rotated at kHz rate to scan in depth only a fraction of the coherence length. In this way frequencies in the MHz range could be generated, sufficient to act as the carrier for the image bandwidth in the T-scan. Two possibilities exist to generate a B-scan:

1. The scanning delay line 10 is driven with a large signal to rotate the mirror 7 sufficient to cover the depth range, the rate of this signal being the frame rate, much smaller than the kHz rate rate of the little amplitude signal applied to create the carrier;

2. Other means are used to scan the path difference in depth, as shown in FIG. 10, where for illustration only, the stage 40 moves the fiber end and lens 28, while 10 is used to generate the phase modulation only. Other possibilities exist, as can be realised by the skillful in the art, which could be applied either in the reference or in the object arm of the interferometer.

C-Scan

C-scans are made from many T-scans along either of X, Y, $\rho$ or $\phi$ coordinates, repeated for different values of the other transverse coordinate, Y, X, $\phi$ or $\rho$ respectively in the transverse plane. The repetition of T-scans along the other transverse coordinate is performed at a slower rate (FIG. 9 bottom), which determines the frame rate. In this way, a complete raster is generated. Different transversal slices are collected for different depths Z, either by advancing the optical path difference in the OCT via the scanning delay line 10 in steps after each complete transverse (XY) or ($\rho,\phi$) scan, or continuously at a much slower speed than the frame rate.

For the the T-scan based B-scan and C-scan regime, the carrier for the square root of reflectivity is created by either the:

a. Phase modulation introduced by the external phase modulator 25, in which case 21 contains a band pass filter tuned on the frequency of the signal applied by driver 26;

b. Phase modulation introduced by the scanning delay line 10, used with the incident beam offset from the axis and driven with a little amplitude signal at KHz rate, in which case 21 contains a band pass filter tuned on the frequency generated by 10;

c. Phase modulation generated by the transverse scanner or scanners in the transverse scanning head 16 determining the line in the final image. In this case, the modulation frequency covers a large range of frequencies starting from zero Hz. In order to reduce the 1/f noise, a high pass filter is used in 21 after photodetection.

FIG. 10 shows an embodiment where a second scanning means, 40, is used to alter the optical path difference. The three cases above, 1, 2, and 3 are applicable to the embodiment in FIG. 10, where the scanning in depth could be achieved using either the scanning delay line 10 similar to the embodiment in FIG. 7 or by using the second scanning means, 40, The scanning delay line 10 refers here to any transmissive scanning delay line which for the scope of functionality of the embodiment in FIG. 10 could be used at low or high data rates, rate similar to that of the transverse scanner 16. The second scanning means could be any form of translation stage, combination of galvanometer scanners such as described in U.S. Pat. No. 5,975,697, a PC controlled translation stage as in U.S. Pat. No. 5,975,697, a voice coil or another form of spectral scanning delay line. Such a configuration preferably performs the depth scanning using the second depth scanning means and uses the spectral delay line 10 for phase modulation only, although other possibilities exist, as exemplified above and hereafter. The second scanning means could be placed in the object as well as in the reference arm, where for the sake of example is shown in FIG. 10 in the reference beam and actuating on one of the fibre end and lens 28.

Figure 11A:
FIG. 11 shows B-scan images obtained with an OCT system similar to that in FIG. 1, where either A-scans or T-scans are used.
Figure 11B:
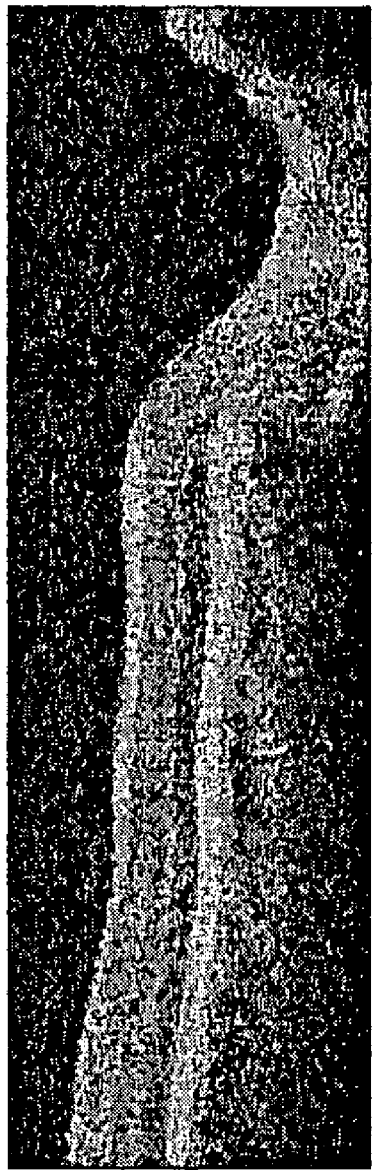

Similar data rate of the scanning delay line means that it is possible to use the same adjustment in the demodulator 21, ie the same high pass filter to demodulate either A-scans or T-scans. Such adjustment allows the same system to be easily and quickly switched from A-scan to T-scan as shown schematically in FIG. 10, where the switch 31 is used to switch the ramp signal from the generator 32 to drive either the scanning delay line 10 or the 2D transverse scanner 16. Two possibilities exist:

a. If the scanning delay line 10 is a spectral scanning delay line, this is adjusted on zero carrier frequency. In this case, a high pass filter is used in 21 and this could have the same characteristics for both positions of the switch 31. When the generator 32 drives the transverse scanner 16, then T, B and C-scans are created based on the phase modulation due to the transverse scanner only. When the generator 32 drives the scanning delay line 10, then A and B-scans are created based on the phase modulation due to the axial scanning only. As explained above, A scans (when 32 drives 100) and T-scans (when 32 drives 16) may look distorted from specular reflectors, but they are close to reality when the sample is a collection of small scattering centers. FIGS. 11a and 11b show B-scan images from the retina obtained in this regime, 11a using T-scans and 11b, using A-scans, where the only difference was switching the two signals, one of 500 Hz and the other of 2 Hz between 10 and 23. In 11a, the line scanner of the scanning head 16 was driven with a ramp at 500 Hz and the scanning delay line 10 was driven with a ramp at 2 Hz. In 11b, the 500 Hz ramp was applied to 10 and the ramp of 2 Hz was applied to the line scanner in 16. The same high pass filter, transmitting frequencies over 10 kHz was used for both regimes. No external phase modulation was implemented and the beam was incident on the axis of rotation of the galvanometer scanner 4, i.e. the spectral delay line in FIG. 1 was on zero frequency carrier. The images 11a and 11b are similar, the depth resolution is limited in both by the coherence length of the source, ~12 microns using a SLD on 810 nm, irrespective of the way the B-scan was built, from T-scans in 11a and from A-scans in 11b. The transverse resolution is also the same, given by the numerical aperture of the interface optics, ~15 microns, irrespective of the scanning sequence used.

b. An external phase modulator 25 (or using the beating of carriers from two external phase modulators) is used to create a high frequency carrier. In this case, a band pass filter is used in 21, tuned on the carrier frequency applied to 25 or by the beating of the two signals applied to the two phase modulators when two such phase modulators are used.

In both cases above, the advancement of the path difference is at a slower rate, either in steps or continuously applied to the spectral scanning delay line from the controlling unit 60, which could be a digital board in a PC.

In the B-scan regime, 60 advances the path actuating on 10 stepwise after each transverse scan (T-scan), or advances the depth continuously, where preferably the advancement during the line period is less or comparable to the coherence length of the optical source used, when evaluated within the sample. In the C-scan, 60 controls at a slower rate the transverse scanning head 16 to generate the frame movement, to obtain a C-scan image. The controlling unit 60 advances the path in 10 stepwise after each C-scan is complete, or advances the depth continuously, where preferably the advancement during the frame period is less or comparable to the coherence length of the optical source used, when evaluated within the sample.

The images 11a and 11b are similar apart from the effect of movement. Axial movement distorts and waves the image in FIG. 11b along the depth coordinate, while transverse movement along the direction of the lateral scanning distorts and waves the image in FIG. 11a along the lateral coordinate. The effect of movement is the same if external phase modulation is used or the scanning delay line 10 is used to generate a carrier. Therefore, such a system could be successfully used in obtaining B-scan images with different imprints of the movement effects. This is useful in imaging moving organs, such as the eye. With such a system, an ophthalmologist could collect the same part of the retina or cornea using A-scan, by controlling fast the scanning delay line or T-scans, by controlling fast the transverse scanner and avoid in each case some, but a different type of movement. By comparing such B-scan images, obtained in two different regimes, information on the movement can be obtained as well as better identify the movement effects.

Persons skilled in the art with the benefit of this disclosure will realize that the same combination of scanning regimes presented above in connection to FIG. 9 could be achieved using a spectral scanning delay line in reflection in a different OCT configuration than that illustrated in FIGS. 7 and 10, and the incorporation of 10 in the recirculating reference beam configuration in FIG. 10 was for the sake of example only.

It should also be evident that all the above in relation to FIGS. 7 and 10 are equally applicable to the OCT channel in any combination of OCT with other imaging procedures, such as a combination OCT/confocal system as disclosed in the U.S. Pat. No. 5,975,697 and U.S. Pat. No. 6,769,769, Optical mapping apparatus with adjustable depth resolution and multiple functionality. This is especially suitable for the eye examination, in which case all comments above in relation to the OCT image could be replicated for the pair of OCT image and confocal image in all scanning regimes, A, T, B and C.

Also, it should be obvious for those skilled in the art of electronics that when working with zero frequency carrier generated by the transverse scanners 16 or spectral delay line, 10, the said high pass filter could be implemented by a large band band pass filter in 21, with the condition that the low frequency cut-off is 10 times larger than the fastest scanning rate, be either the transverse scanning or the depth scanning. A cut-off at high frequency naturally exists due to the electronic bandwidth of components and this should be brought down to the value of image bandwidth in order to reduce the noise. Alternatively, two band pass filters could be used, for instance one between 10 and 50 kHz and another one from 50 to 100 kHz to cover the band of 10 to 100 kHz. The signals output of these two filters is each first rectified and then summed or squared to produce the signal to be sent to displaying device 43.

All references referred to in this specification are herein incorporated by reference in their entirety.

We claim:

1. A scanning delay line for use in optical coherence tomography apparatus, comprising:
    an input port for admitting a collimated input beam;
    an output port for launching an output beam;
    a tiltable mirror;
    optical convergence means for converging light incident thereon;
    dispersive means for dispersing light incident thereon; and
    redirecting means for changing the direction of a beam incident thereon; and
    wherein said tiltable mirror, said optical convergence means, said dispersive means, and said redirecting means are arranged in an optical configuration such that in sequence:
    said dispersive means directs said input beam toward said optical convergence means;
    said optical convergence means directs said input beam received from said dispersive means toward said tiltable mirror;
    said tiltable mirror reflects said input beam received from said optical convergence means as a first return beam back toward said optical convergence means;
    said optical convergence means directs said first return beam received from said tiltable mirror toward said dispersive means;
    said dispersive means directs said first return beam received from said optical convergence means toward said redirecting means; and
    said redirecting means redirects said first return beam received from said dispersive means toward said tiltable mirror via said optical convergence means and bypassing said dispersive means and in a direction such that said tiltable mirror reflects said first return beam received from said dispersive means via said optical convergence means back toward said optical convergence means as a second return beam and said optical convergence means directs said second return beam received from said tiltable mirror toward said output port as part of an output beam bypassing said dispersive means and such that said output beam lies along substantially the same axis regardless of the angle of tilt of said tiltable mirror; and whereby tilting said mirror introduces a variable optical delay between said input and output ports.

2. A scanning delay line as claimed in claim 1, wherein said optical convergence means comprises a common optical convergence element that directs said input beam received from said dispersion means toward said tiltable mirror, that directs said first return beam received from said tiltable mirror toward said dispersive means, that directs said first return beam received from said dispersive means toward said tiltable mirror, and directs said second return beam toward said output port.

3. A scanning delay line as claimed in claim 2, wherein said common optical convergence element comprises a lens.

4. A scanning delay line as claimed in claim 2, wherein said dispersive means comprises a common dispersive element that directs said input beam toward said optical convergence means and directs said first return beam toward said redirecting means.

5. A scanning delay line as claimed in claim 4, wherein said common dispersive element comprises a diffraction grating.

6. A scanning delay line as claimed in claim 4, wherein said common dispersive element comprises a prism.

7. A scanning delay line as claimed in claim 4, wherein said redirecting means comprises mirror means.

8. A scanning delay line as claimed in claim 7, wherein said mirror means comprise a pair of mirrors oriented to reflect light spectrally dispersed from said common dispersive element and to launch said spectrally dispersed light through said common optical convergence element toward said tiltable mirror for des canning lateral movement of the output beam.

9. A scanning delay line as claimed in claim 8, wherein said pair of mirrors launches said spectrally dispersed light into said optical convergence element at an incidence point which, in relation to a central optical axis of said optical convergence element, is at an opposite side of said optical convergence relative to a point of emergence of said first return beam.

10. A scanning delay line as claimed in claim 1, further comprising at least one telescope comprising a pair of lenses in the first return beam between said dispersive means and said optical convergence means.

11. A scanning delay line as claimed in claim 1, wherein said optical convergence means comprise separate first and second optical convergence elements, and wherein said first optical convergence element directs said first return beam toward said dispersive means, and said second optical convergence element receives said first return beam from said redirecting means, said redirecting means directs said first return beam toward a back side of said tiltable mirror, and said tiltable mirror returns said first return beam via said second optical convergence element as said output beam toward said output port.

12. A scanning delay line as claimed in claim 1, wherein said dispersive element comprises a prism, said input beam is directed through said prism toward said optical convergence means, and said first return beam passes through said prism toward said redirecting means.

13. A scanning delay line as claimed in claim 1, wherein said optical convergence means comprises a first curved mirror that directs said input beam toward said tiltable mirror and directs said first return beam toward said dispersive means, and a second curved mirror that directs said second return beam toward said output port.

14. A scanning delay line as claimed in claim 1, wherein said dispersive means comprises first and second dispersive elements, and said optical convergence means comprise first, second, third, and fourth curved mirrors, and wherein said first dispersive element directs said input beam to said first curved mirror, said first curved mirror directs said input beam toward said tiltable mirror, said second curved mirror directs said first return beam toward said second dispersive element, said second dispersive element directs said first return beam toward said redirecting means, said redirecting means directs said first return beam toward said third curved mirror, said third curved mirror directs said first return beam toward a backside of said tiltable mirror, and said fourth curved mirror directs said second return beam from the backside of said tiltable mirror toward said output port.

15. A scanning delay line as claimed in claim 14, wherein said first and second dispersive elements are diffraction gratings.

16. A scanning delay line as claimed in claim 1, wherein the tiltable mirror is a scanning galvanometer, and wherein said scanning galvanometer scans said input beam incident thereon, and descans said first return beam incident thereon.

17. An apparatus for performing optical coherence tomography on a sample, comprising an interferometer incorporating a scanning delay line according to claim 1, a low coherence source driving said interferometer, a photodetection unit for detecting an output signal from said interferometer, an electronic processing unit for processing said output signal, a scanner for scanning the sample angularly or transversally, interface optics for conveying the scanned beam to the sample, and a display means for displaying the OCT image, wherein said scanning delay line and said scanner are synchronized with said display means.

18. An apparatus according to claim 17, wherein said scanning delay line and said scanner are configured to generate fast A-scans or B-scans by scanning the scanning delay line fast and said scanner slowly, wherein the display means displays a raster having lines corresponding to movement of the scanning delay line.

19. An apparatus according to claim 17, wherein said tiltable mirror is tiltable about an axis of rotation, and said input beam is incident on said tiltable mirror off said axis of rotation, whereby a high frequency carrier is generated as a result of said input beam being incident on said tiltable mirror off said axis of rotation, and wherein said electronic processing unit comprises an electronic bandpass filter tuned on such high frequency.

20. An apparatus for optical coherence tomography according to claim 17, further comprising an external phase modulator in tandem with said scanning delay line, and wherein said electronic processing unit comprises an electronic bandpass filter tuned on the frequency generated by the external phase modulator.

21. An apparatus according to claim 17, wherein said scanning delay line is driven by a ramp signal, said processing unit comprises a high pass filter with a frequency cut-off at least ten times greater than the frequency of said ramp signal.

22. An apparatus according to claim 17, wherein said scanning delay line and said scanner are configured to generate T-scans or B-scans by scanning the scanning delay line slowly and said scanner fast, wherein the display means displays a raster having lines corresponding to movement of the scanner.

23. An apparatus according to claim 17, wherein said scanning delay line and said scanner are configured to generate stacks of C-scans at different depths by generating first a raster of a C-scan by controlling the scanner followed by movement of the scanning delay line to a new depth position and to repeat the collecting of a C-scan raster until the desired number of C-scans are collected.

24. An apparatus according to claim 17, wherein said scanner is configured to generate stacks of C-scans at different depths by acquiring rasters by controlling the scanner while the scanning delay line is moved continuously at a pace much slower than that of completing a given said raster until all depth range has been scanned by the scanning delay line.

25. An apparatus according to claim 20, further comprising a phase modulator in tandem with said scanning delay line, said phase modulator being driven at a sufficiently high frequency to modulate an interference signal generated by said interferometer, and wherein said electronic processing unit consists of an electronic bandpass filter tuned on the frequency induced by the external phase modulator.

26. An apparatus according to claim 24, wherein a phase modulation of the interference signal is generated by said scanner, and the processing unit consists of a high pass filter with a frequency cut-off at least ten times greater than the frequency of a ramp signal driving said scanner in said scanner.

27. An apparatus according to claim 21, which is configured such that the same high pass filter is used in both A based B-scans and T-based B-scans.

28. A method of varying the optical path length of an incident light beam, comprising:
   directing a collimated input beam toward dispersive means;
   directing light from said dispersive means toward a tiltable mirror for a first pass via optical convergence means;
   returning light from said tiltable mirror via said optical convergence means toward said dispersive means;
   directing said returned light from said dispersive means toward redirecting means;
   directing said light from said redirecting means via said optical convergence means and bypassing said dispersive means toward said tiltable mirror for a second pass;
   returning light reflected a second time via said optical convergence means toward an output port as an output beam bypassing said dispersive means; and
   tilting said mirror to vary the optical path length of said incident light beam between the input port and output port while maintaining substantially the same axis of said output beam.

29. A method as claimed in claim 28, wherein said dispersive means is a diffraction grating.

30. A method as claimed in claim 28, wherein light returning from said dispersive means via the redirecting means to said tiltable mirror passes through a pair of telescopes, each comprising a pair of lenses.

31. A method as claimed in claim 30, wherein said dispersive means is a prism.

32. A method as claimed in claim 28, wherein said tiltable mirror is a scanning galvanometer, which scans said light on said first pass and descans said light on said second pass.

* * * * *